United States Patent
Hur et al.

(10) Patent No.: US 11,466,131 B2
(45) Date of Patent: Oct. 11, 2022

(54) SUPERABSORBENT POLYMER AND PREPARATION METHOD THEREOF

(71) Applicant: LG Chem, Ltd., Seoul (KR)

(72) Inventors: Young Jae Hur, Daejeon (KR); Dae Woo Nam, Daejeon (KR); Bohee Park, Daejeon (KR); Sujin Kim, Daejeon (KR)

(73) Assignee: LG Chem, Ltd.

( * ) Notice: Subject to any disclaimer, the term of this patent is extended or adjusted under 35 U.S.C. 154(b) by 0 days.

(21) Appl. No.: 16/756,921

(22) PCT Filed: Sep. 17, 2019

(86) PCT No.: PCT/KR2019/011994
§ 371 (c)(1),
(2) Date: Apr. 17, 2020

(87) PCT Pub. No.: WO2020/101167
PCT Pub. Date: May 22, 2020

(65) Prior Publication Data
US 2021/0147640 A1   May 20, 2021

(30) Foreign Application Priority Data

Nov. 13, 2018 (KR) .......... 10-2018-0139103
Sep. 16, 2019 (KR) .......... 10-2019-0113734

(51) Int. Cl.
| | |
|---|---|
| *A61L 15/60* | (2006.01) |
| *C08J 3/24* | (2006.01) |
| *A61L 15/24* | (2006.01) |
| *B01J 20/02* | (2006.01) |
| *B01J 20/10* | (2006.01) |
| *B01J 20/26* | (2006.01) |
| *B01J 20/30* | (2006.01) |
| *C08F 220/06* | (2006.01) |
| *C08J 3/075* | (2006.01) |
| *C08J 3/12* | (2006.01) |
| *C08K 3/36* | (2006.01) |

(52) U.S. Cl.
CPC ............. *C08J 3/245* (2013.01); *A61L 15/24* (2013.01); *A61L 15/60* (2013.01); *B01J 20/0281* (2013.01); *B01J 20/103* (2013.01); *B01J 20/267* (2013.01); *B01J 20/3021* (2013.01); *C08F 220/06* (2013.01); *C08J 3/075* (2013.01); *C08J 3/12* (2013.01); *C08K 3/36* (2013.01); *B01J 2220/46* (2013.01); *B01J 2220/68* (2013.01); *C08J 2333/02* (2013.01)

(58) Field of Classification Search
CPC ..... C08J 3/245; C08J 3/075; C08J 3/12; C08J 2333/02; C08J 2333/08; C08J 2333/10; C08J 3/24; C08J 3/246; C08J 2300/14; A61L 15/24; A61L 15/60; B01J 20/0281; B01J 20/103; B01J 20/267; B01J 20/3021; B01J 2220/46; B01J 2220/68; C08F 220/06; C08F 2/50; C08F 2/44; C08F 2810/20; C08K 3/36; C08K 3/013; C08K 3/12; C08K 5/098; C08K 5/10; C08K 5/1515

See application file for complete search history.

(56) References Cited

U.S. PATENT DOCUMENTS

| | | | |
|---|---|---|---|
| 625,488 | A | 5/1899 | Auspitz |
| 4,587,308 | A * | 5/1986 | Makita ............ A61L 15/60 524/430 |
| 4,734,478 | A | 3/1988 | Tsubakimoto et al. |
| 4,755,562 | A | 7/1988 | Alexander et al. |
| 4,806,578 | A | 2/1989 | Kobayashi et al. |
| 4,824,901 | A | 4/1989 | Alexander et al. |
| 5,096,944 | A | 3/1992 | Itou et al. |
| 5,112,902 | A | 5/1992 | Moriya et al. |
| 5,610,208 | A | 3/1997 | Dairoku et al. |
| 5,669,894 | A | 9/1997 | Goldman et al. |
| 5,672,633 | A | 9/1997 | Brehm et al. |
| 5,840,321 | A | 11/1998 | Engelhardt et al. |
| 6,239,230 | B1 | 5/2001 | Eckert et al. |
| 6,265,488 | B1 | 7/2001 | Fujino et al. |
| 6,297,319 | B1 | 10/2001 | Nagasuna et al. |
| 6,372,852 | B2 | 4/2002 | Hitomi et al. |
| 6,472,478 | B1 | 10/2002 | Funk et al. |
| 6,559,239 | B1 | 5/2003 | Riegel et al. |
| 6,605,673 | B1 | 8/2003 | Mertens et al. |
| 6,620,899 | B1 | 9/2003 | Morken et al. |
| 6,657,015 | B1 | 12/2003 | Riegel et al. |

(Continued)

FOREIGN PATENT DOCUMENTS

| | | |
|---|---|---|
| DE | 19630131 A1 | 3/1997 |
| EP | 0532002 A1 | 3/1993 |

(Continued)

OTHER PUBLICATIONS

Translation of JP 2008297512 (Year: 2008).*
Translation of JPH10-244151 (Year: 1998).*
International Search Report for Application No. PCT/KR2019/011994 dated Jan. 10, 2020. 2 pages.
Odian, Principles of Polymerization, Second Edition, Copyright 1981 by John Wiley & Sons, Inc, p. 203.
Schwalm, UV Coatings; Basics, Recent Developments and New Applications, Dec. 21, 2006, p. 115, Elsevier Science.

(Continued)

*Primary Examiner* — Robert C Boyle
(74) *Attorney, Agent, or Firm* — Lerner, David, Littenberg, Krumholz & Mentlik, LLP

(57) ABSTRACT

Provided are a superabsorbent polymer and a preparation method thereof, including preparing a base resin and conducting surface modification of the base resin in the presence of an inorganic filler. The method of preparing the superabsorbent polymer of the present invention may provide a superabsorbent polymer having improved rewetting property and liquid permeability.

14 Claims, No Drawings

(56) References Cited

U.S. PATENT DOCUMENTS

| | | | |
|---|---|---|---|
| 6,809,158 B2 | 10/2004 | Ikeuchi et al. | |
| 7,833,624 B2 | 11/2010 | Harren et al. | |
| 2003/0207997 A1 | 11/2003 | Mertens et al. | |
| 2004/0106745 A1 | 6/2004 | Nakashima et al. | |
| 2004/0214946 A1* | 10/2004 | Smith | A61L 15/60 524/556 |
| 2005/0048221 A1 | 3/2005 | Irie et al. | |
| 2005/0118423 A1 | 6/2005 | Adachi et al. | |
| 2005/0137546 A1 | 6/2005 | Joy et al. | |
| 2005/0209352 A1 | 9/2005 | Dairoku et al. | |
| 2008/0221229 A1 | 9/2008 | Torii et al. | |
| 2009/0191408 A1 | 7/2009 | Tian et al. | |
| 2011/0301560 A1 | 12/2011 | Fujimura et al. | |
| 2012/0295103 A1 | 11/2012 | Kikuno et al. | |
| 2013/0187089 A1 | 7/2013 | Daniel et al. | |
| 2014/0364824 A1 | 12/2014 | Ota et al. | |
| 2015/0129799 A1 | 5/2015 | Kobayashi et al. | |
| 2015/0217270 A1 | 8/2015 | Ueda et al. | |
| 2015/0273433 A1 | 10/2015 | Nakatsuru et al. | |
| 2015/0283284 A1 | 10/2015 | Azad et al. | |
| 2016/0060418 A1 | 3/2016 | Tian et al. | |
| 2016/0208035 A1 | 7/2016 | Ryu et al. | |
| 2016/0288088 A1 | 10/2016 | Kim et al. | |
| 2016/0354757 A1 | 12/2016 | Lee et al. | |
| 2016/0361703 A1 | 12/2016 | Jang et al. | |
| 2016/0367965 A1 | 12/2016 | Kim et al. | |
| 2016/0375171 A1 | 12/2016 | Omori et al. | |
| 2017/0210831 A1 | 7/2017 | Hinayama et al. | |
| 2017/0216817 A1 | 8/2017 | Torii et al. | |
| 2018/0037686 A1 | 2/2018 | Lee et al. | |
| 2018/0044487 A1 | 2/2018 | Miyajima et al. | |
| 2018/0243464 A1 | 8/2018 | Hwang et al. | |
| 2018/0244857 A1 | 8/2018 | Lee et al. | |
| 2018/0298132 A1 | 10/2018 | Yorino et al. | |
| 2019/0099739 A1 | 4/2019 | Lee et al. | |
| 2019/0111411 A1 | 4/2019 | Torii et al. | |
| 2020/0009529 A1 | 1/2020 | Nam et al. | |
| 2020/0010624 A1 | 1/2020 | Nam et al. | |
| 2020/0116172 A1 | 4/2020 | Sun | |
| 2020/0122119 A1 | 4/2020 | Jeong et al. | |
| 2020/0308352 A1 | 10/2020 | Park et al. | |
| 2021/0069674 A1 | 3/2021 | Jung et al. | |
| 2021/0147640 A1 | 5/2021 | Hur et al. | |
| 2022/0080387 A1 | 3/2022 | Hur et al. | |

FOREIGN PATENT DOCUMENTS

| | | |
|---|---|---|
| EP | 0755964 A2 | 1/1997 |
| EP | 0752892 B1 | 7/2001 |
| EP | 1694372 A1 | 8/2006 |
| EP | 2127741 A1 | 12/2009 |
| EP | 2377897 A1 | 10/2011 |
| EP | 2484439 A1 | 8/2012 |
| EP | 2797638 A1 | 11/2014 |
| EP | 2891520 A1 | 7/2015 |
| EP | 2905072 A1 | 8/2015 |
| EP | 3085439 A1 | 10/2016 |
| EP | 2877137 B1 | 5/2017 |
| EP | 3202823 A1 | 8/2017 |
| EP | 3527611 A1 | 8/2019 |
| JP | H02170808 A | 7/1990 |
| JP | H03064301 A | 3/1991 |
| JP | H03192142 A | 8/1991 |
| JP | H05507511 A | 10/1993 |
| JP | H0639485 B2 | 5/1994 |
| JP | H07010923 A | 1/1995 |
| JP | H08157531 A | 6/1996 |
| JP | H08157606 A | 6/1996 |
| JP | H10-244151 * | 9/1998 |
| JP | H10244151 A | 9/1998 |
| JP | H11310644 A | 11/1999 |
| JP | 2002538275 A | 11/2002 |
| JP | 2004261796 A | 9/2004 |
| JP | 2006057075 A | 3/2006 |
| JP | 2007514833 A | 6/2007 |
| JP | 2008178667 A | 8/2008 |
| JP | 2008297512 * | 12/2008 |
| JP | 2009051952 A | 3/2009 |
| JP | 2009203383 A | 9/2009 |
| JP | 2011080069 A | 4/2011 |
| JP | 2011511136 A | 4/2011 |
| JP | 2011252080 A | 12/2011 |
| JP | 2012007062 A | 1/2012 |
| JP | 201250832 A | 12/2012 |
| JP | 5162160 B2 | 3/2013 |
| JP | 2013132434 A | 7/2013 |
| JP | 2013213083 A | 10/2013 |
| JP | 2014108165 A | 6/2014 |
| JP | 2015091586 A | 5/2015 |
| JP | 2015178099 A | 10/2015 |
| JP | 2016028131 A | 2/2016 |
| JP | 2016035060 A | 3/2016 |
| JP | 2017500381 A | 1/2017 |
| JP | 6092228 B2 | 3/2017 |
| JP | 2017185485 A | 10/2017 |
| JP | 2017206646 A | 11/2017 |
| JP | 2020518768 A | 6/2020 |
| JP | 2020528394 A | 9/2020 |
| KR | 890009993 A | 8/1989 |
| KR | 100336706 B1 | 12/2002 |
| KR | 100858387 B1 | 9/2008 |
| KR | 20110114535 A | 10/2011 |
| KR | 20150048785 A | 5/2015 |
| KR | 20150066454 A | 6/2015 |
| KR | 20150067218 A | 6/2015 |
| KR | 20160063956 A | 6/2016 |
| KR | 20160067725 A | 6/2016 |
| KR | 20160076422 A | 6/2016 |
| KR | 20160081533 A | 7/2016 |
| KR | 20170020113 A | 2/2017 |
| KR | 20170106799 A | 9/2017 |
| KR | 20170111295 A | 10/2017 |
| KR | 20180019558 A | 2/2018 |
| KR | 20180040404 A | 4/2018 |
| KR | 20180067943 A | 6/2018 |
| WO | 9118042 A1 | 11/1991 |
| WO | 2004096304 A1 | 11/2004 |
| WO | 2006078046 A2 | 7/2006 |
| WO | 2010073658 A1 | 7/2010 |
| WO | 2014054731 A1 | 4/2014 |
| WO | 2016052537 A1 | 4/2016 |
| WO | 2016143739 A1 | 9/2016 |
| WO | 2017170605 A1 | 10/2017 |
| WO | 2018110758 A1 | 6/2018 |
| WO | 2018110760 A1 | 6/2018 |
| WO | 2018117390 A1 | 6/2018 |
| WO | 2018147317 A1 | 8/2018 |
| WO | 2019018670 A1 | 1/2019 |

OTHER PUBLICATIONS

European Search Report for Application No. EP18888466, dated Nov. 19, 2020, 6 pages.
European Search Report for Application No. EP19863965, dated Nov. 30, 2020, 6 pages.
International Search Report for Application No. PCT/KR2018/014840 dated Mar. 11, 2019, 5 pages.
Third Party Observation for EP19863965.0, dated Jan. 26, 2021, 4 pages.
Third Party Observation for PCT/KR2018/014840 submitted on Mar. 4, 2020, 16 pages.
Third Party Observation for Application No. PCT/KR2019/011994 submitted Mar. 8, 2021, pp. 1-13.
Taiyo Kagaku, "How to use HLB Values," Aug. 2016, pp. 1-8. https://www.taiyokagaku.com/lab/emulsion_learning/06/.
Buchholz, F.L., & Graham, A.T., "Modern superabsorbent polymer technology". Wiley-VCH (1998) 41 pgs.
"Test Transcript", Nippon Shokubai Co., Ltd. (May 2022). 8 pgs.
Denacol Catalog, Epoxy Compound, Nagase Kasei Kogyo Co., Ltd. (1998) 9 pgs.

(56) References Cited

OTHER PUBLICATIONS

Japanese Industrial Standard, "Testing method for water absorption rate of super absorbent polymers," Mar. 1, 1996, 25 pages, Tokyo, Japan. [Providing English Translation of Abstract only].
Data sheet for the decision of Appeal, EP0532002, T0137/01, Dec. 15, 2003 (European Patent Office), 23 pages.
Third Party Observation for Application No. EP 18888466.2 dated Jun. 23, 2022, pp. 1-7.

\* cited by examiner

SUPERABSORBENT POLYMER AND PREPARATION METHOD THEREOF

CROSS-REFERENCE TO RELATED APPLICATIONS

The present application is a national phase entry under 35 U.S.C. § 371 of International Application No. PCT/KR2019/011994, filed on Sep. 17, 2019, which claims priority from, Korean Patent Application No. 10-2018-0139103, filed on Nov. 13, 2018 and Korean Patent Application No. 10-2019-0113734, filed on Sep. 16, 2019, the disclosures of which are hereby incorporated by reference in their entirety.

TECHNICAL FIELD

The present invention relates to a superabsorbent polymer and a preparation method thereof. More particularly, the present invention relates to a superabsorbent polymer having improved rewetting property and liquid permeability, and a preparation method thereof.

BACKGROUND ART

A superabsorbent polymer (SAP) is a synthetic polymeric material capable of absorbing moisture from 500 to 1000 times its own weight. Various manufacturers have denominated it as different names, such as SAM (Super Absorbency Material), AGM (Absorbent Gel Material), etc. Since such superabsorbent polymers started to be practically applied in sanitary products, now they have been widely used not only for hygiene products such as disposable diapers for children, sanitary pads, etc., but also for water retaining soil products for gardening, water stop materials for the civil engineering and construction, sheets for raising seedling, fresh-keeping agents for food distribution fields, materials for poultice or the like.

In most cases, these superabsorbent polymers have been widely used in the field of hygienic materials such as diapers, sanitary pads, etc. For these applications, superabsorbent polymers are required to exhibit high absorbency with respect to water, etc., not to release the absorbed water even under an external pressure, and also to well maintain their shape even in a state where the volume is expanded (swelled) by absorbing water, thereby exhibiting excellent liquid permeability.

Reportedly, it is difficult to improve, at the same time, centrifuge retention capacity (CRC), which is a basic physical property representing the water absorption and retention capacities of the superabsorbent polymer, and absorbency under pressure (AUP), which represents a property of retaining absorbed water even under an external pressure. The reason is that when the overall crosslinking density of the superabsorbent polymer is controlled to be low, centrifuge retention capacity becomes relatively high, but a crosslinking structure becomes loose and gel strength becomes low, leading to a reduction in absorbency under pressure. On the contrary, when the crosslinking density is controlled to be high, and therefore absorbency under pressure is improved, water is hardly absorbed between compact crosslinking structures, leading to a reduction in basic centrifuge retention capacity. Because of the above-described reasons, there have been limitations in providing superabsorbent polymers in which centrifuge retention capacity and absorbency under pressure are improved at the same time.

Recently, as hygiene materials such as diapers or sanitary pads become thinner, superabsorbent polymers are required to have higher absorption performance. Of them, simultaneous enhancement of centrifuge retention capacity and absorbency under pressure which are incompatible physical properties, and improvement of liquid permeability are emerging as important issues.

Further, a pressure by a user's weight may be applied to hygiene materials such as diapers, sanitary pads, etc. In particular, when liquid is absorbed by the superabsorbent polymer used in hygiene materials such as diapers, sanitary pads, etc., and then a pressure by a user's weight is applied thereto, a rewetting phenomenon, in which some liquid absorbed into the superabsorbent polymer leaks out again, and a urine leakage phenomenon may occur.

Accordingly, various attempts have been made to suppress such a rewetting phenomenon. However, concrete methods capable of effectively suppressing the rewetting phenomenon have not yet been suggested.

DISCLOSURE

Technical Problem

To solve the above problems of the prior art, an object of the present invention is to provide a superabsorbent polymer suppressing rewetting and urine leakage phenomena, and a preparation method thereof.

Technical Solution

To achieve the above object, an aspect of the present invention provides a method of preparing a superabsorbent polymer, the method including the steps of:

preparing a base resin by crosslinking polymerization of an acrylic acid-based monomer having acidic groups, of which at least a part is neutralized, and an internal crosslinking agent (step 1);

mixing the base resin with an inorganic filler and an epoxy-based surface crosslinking agent, in which the base resin is first dry-mixed with the inorganic filler, and subsequently, mixed with the epoxy-based surface crosslinking agent in the form of a surface crosslinking solution by dissolving it in water (step 2); and performing surface modification of the base resin by raising the temperature of the mixture of step 2 (step 3), wherein the epoxy-based surface crosslinking agent includes a first epoxy crosslinking agent having an epoxy equivalent weight of 100 g/eq or more to less than 130 g/eq and a second epoxy crosslinking agent having an epoxy equivalent weight of 130 g/eq to 200 g/eq.

Further, another aspect of the present invention provides a superabsorbent polymer including a base resin including a crosslinked polymer which is prepared by crosslinking polymerization of an acrylic acid-based monomer having acidic groups, of which at least a part is neutralized; and a double surface-modified layer which is formed on the particle surface of the base resin, and is prepared by additionally crosslinking the crosslinked polymer via two kinds of epoxy-based surface crosslinking agents having different epoxy equivalent weights, wherein the surface-modified layer includes an inorganic filler, and the two kinds of epoxy-based surface crosslinking agents include a first epoxy crosslinking agent having an epoxy equivalent weight of 100 g/eq or more to less than 130 g/eq and a second epoxy crosslinking agent having an epoxy equivalent weight of 130 g/eq to 200 g/eq.

Effect of the Invention

According to a superabsorbent polymer and a preparation method thereof of the present invention, provided is a superabsorbent polymer suppressing a rewetting phenomenon and a urine leakage phenomenon while exhibiting excellent absorption properties.

BEST MODE FOR CARRYING OUT THE INVENTION

While the present invention is susceptible to various modifications and alternative forms, specific embodiments will be illustrated and described in detail as follows. It should be understood, however, that the description is not intended to limit the present invention to the particular forms disclosed, but on the contrary, the intention is to cover all modifications, equivalents, and alternatives falling within the spirit and scope of the invention.

Hereinafter, a method of preparing a superabsorbent polymer according to one embodiment of the present invention will be described in detail.

The method of preparing a superabsorbent polymer according to one embodiment of the present invention includes the steps of:

preparing a base resin by crosslinking polymerization of an acrylic acid-based monomer having acidic groups, of which at least a part is neutralized, and an internal crosslinking agent (step 1);

mixing the base resin with an inorganic filler and an epoxy-based surface crosslinking agent, in which the base resin is first dry-mixed with the inorganic filler, and subsequently, mixed with the epoxy-based surface crosslinking agent in the form of a surface crosslinking solution by dissolving it in water (step 2); and performing surface modification of the base resin by raising the temperature of the mixture of step 2 (step 3), wherein the epoxy-based surface crosslinking agent includes a first epoxy crosslinking agent having an epoxy equivalent weight of 100 g/eq or more to less than 130 g/eq and a second epoxy crosslinking agent having an epoxy equivalent weight of 130 g/eq to 200 g/eq.

As used herein, the "base resin" or "base resin powder", in the form of particle or powder obtained by drying and pulverizing a polymer resulting from polymerizing a water-soluble ethylene-based unsaturated monomer, refers to a polymer which does not undergo a surface modification or surface crosslinking step described below.

A water-containing gel polymer obtained by polymerization reaction of an acrylic acid-based monomer is marketed as a superabsorbent polymer in a powdery product, after processes such as drying, pulverizing, size-sorting, surface-crosslinking, etc.

Recently, not only absorption properties such as absorbency and liquid permeability of superabsorbent polymers, but also how long surface dryness is maintained in an actual situation where a diaper is used are important measure of diaper characteristics.

It was found that the superabsorbent polymer obtained by the preparation method according to one embodiment of the present invention has excellent physical properties such as centrifuge retention capacity, absorbency under pressure, liquid permeability, etc., thereby exhibiting excellent absorption performances, maintains in a dry state even after being swollen by brine, and effectively prevents rewetting and urine leakage phenomena in which urine absorbed into the superabsorbent polymer leaks out again, thereby completing the present invention.

In the method of preparing the superabsorbent polymer of the present invention, a monomer composition which is a raw material of the superabsorbent polymer includes an acrylic acid-based monomer having acidic groups, of which at least a part is neutralized, an internal crosslinking agent, and a polymerization initiator, and the monomer composition is polymerized to obtain the water-containing gel polymer, which is then dried, pulverized, and size-sorted to prepare the base resin (step 1).

This step will be described in more detail below.

The monomer composition which is a raw material of the superabsorbent polymer includes the acrylic acid-based monomer having acidic groups, of which at least a part is neutralized, and the polymerization initiator.

The acrylic acid-based monomer is a compound represented by the following Chemical formula 1:

$$R^1\text{—COOM}^1 \qquad \text{[Chemical formula 1]}$$

in Chemical Formula 1, $R^1$ is an alkyl group containing an unsaturated bond and having 2 to 5 carbon atoms, and $M^1$ is a hydrogen atom, a monovalent or divalent metal, an ammonium group, or an organic amine salt.

Preferably, the acrylic acid-based monomer may include one or more selected from the group consisting of acrylic acid, methacrylic acid, and a monovalent metal salt thereof, a divalent metal salt thereof, an ammonium salt thereof, and an organic amine salt thereof.

Here, the acrylic acid-based monomer may have acidic groups, of which at least a part is neutralized. Preferably, those partially neutralized with an alkali substance such as sodium hydroxide, potassium hydroxide, ammonium hydroxide, etc. may be used as the monomer. In this regard, a degree of neutralization of the acrylic acid-based monomer may be 40 mol % to 95 mol %, or 40 mol % to 80 mol %, or 45 mol % to 75 mol %. The range of the neutralization degree may vary depending on final physical properties. However, an excessively high degree of neutralization renders the neutralized monomers precipitated, and thus polymerization may not occur readily, whereas an excessively low degree of neutralization not only greatly deteriorates absorbency of the polymer but also endows the polymer with hard-to-handle properties, such as of elastic rubber.

A concentration of the acrylic acid-based monomer may be about 20% by weight to about 60% by weight, preferably about 40% by weight to about 50% by weight with respect to the monomer composition including the raw materials of the superabsorbent polymer and a solvent, and the concentration may be properly controlled, taking into consideration a polymerization time and reaction conditions. However, if the monomer concentration is too low, the yield of the superabsorbent polymer may become low and an economic problem may occur. On the contrary, if the concentration is too high, there is a process problem that a part of the monomers is precipitated, or pulverization efficiency is lowered upon pulverization of the polymerized water-containing gel polymer, and the physical properties of the superabsorbent polymer may be reduced.

In the method of preparing the superabsorbent polymer of the present invention, the polymerization initiator used during polymerization is not particularly limited, as long as it is generally used in the preparation of the superabsorbent polymer.

Specifically, the polymerization initiator may be a thermal polymerization initiator or a photo-polymerization initiator by UV irradiation, depending on a polymerization method. However, even though the photopolymerization is performed, a certain amount of heat may be generated by UV irradiation or the like, and also generated with exothermic polymerization reaction. Therefore, the thermal polymerization initiator may be further included.

As the photo-polymerization initiator, a compound capable of forming radicals by a light such as UV may be used without limitations in the constitution.

For example, one or more selected from the group consisting of benzoin ether, dialkyl acetophenone, hydroxyl alkylketone, phenyl glyoxylate, benzyl dimethyl ketal, acyl phosphine, and α-aminoketone may be used as the photo-polymerization initiator. Meanwhile, as the specific example of acyl phosphine, commercially available lucirin TPO, namely, 2,4,6-trimethyl-benzoyl-trimethyl phosphine oxide may be used. More various photo-polymerization initiators are well disclosed in 'UV Coatings: Basics, Recent Developments and New Application (Elsevier 2007)' written by Reinhold Schwalm, p 115, however, they are not limited to the above described examples.

The photo-polymerization initiator may be included in an amount of about 0.01% by weight to about 1.0% by weight in the monomer composition. If the concentration of the photo-polymerization initiator is too low, the polymerization rate may become low. If the concentration of the photo-polymerization initiator is too high, the molecular weight of the superabsorbent polymer may become low and its physical properties may not be uniform.

Further, one or more selected from the group consisting of persulfate-based initiators, azo-based initiators, hydrogen peroxide, and ascorbic acid may be used as the thermal polymerization initiator. Specific examples of the persulfate-based initiators may include sodium persulfate ($Na_2S_2O_8$), potassium persulfate ($K_2S_2O_8$), ammonium persulfate (($NH_4)_2S_2O_8$) or the like. Examples of the azo-based initiators may include 2,2-azobis(2-amidinopropane)dihydrochloride, 2,2-azobis-(N,N-dimethylene)isobutyramidine dihydrochloride, 2-(carbamoylazo)isobutyronitrile, 2,2-azobis(2-[2-imidazolin-2-yl]propane)dihydrochloride, 4,4-azobis-(4-cyanovaleric acid) or the like. More various thermal polymerization initiators are well-disclosed in 'Principle of Polymerization (Wiley, 1981)' written by Odian, p 203, however, they are not limited to the above described examples.

According to one exemplary embodiment of the present invention, the monomer composition includes the internal crosslinking agent as the raw material of the superabsorbent polymer. The internal crosslinking agent may include a crosslinking agent having one or more ethylenic unsaturated functional groups in addition to one or more functional groups capable of reacting with the acrylic acid-based monomer; or a crosslinking agent having two or more functional groups capable of reacting with the substituents of the acrylic acid-based monomer and/or the substituents formed by hydrolysis of the monomer.

The internal crosslinking agent is for internal crosslinking of the polymer obtained by polymerizing the acrylic acid-based monomer, and it is distinguished from a surface crosslinking agent for surface-crosslinking of the polymer.

Specific examples of the internal crosslinking agent may include one or more selected from the group consisting of N,N'-methylenebisacrylamide, trimethylolpropane tri(meth)acrylate, ethylene glycol di(meth)acrylate, (meth)acrylate, propylene glycol di(meth)acrylate, polypropylene glycol (meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaerythritol pentacrylate, glycerin tri(meth)acrylate, pentaerythritol tetraacrylate, triarylamine, ethylene glycol diglycidyl ether, propylene glycol, glycerin, and ethylene carbonate.

Such an internal crosslinking agent may be added at a concentration of about 0.01% by weight to about 1.0% by weight, with respect to the monomer composition, thereby crosslinking the polymerized polymer.

In the preparation method of the present invention, the monomer composition of the superabsorbent polymer may further include an additive such as a thickener, a plasticizer, a preservation stabilizer, an antioxidant, etc., if necessary.

The raw materials such as the above-described acrylic acid-based monomer having acidic groups, of which at least a part is neutralized, photo-polymerization initiator, thermal polymerization initiator, internal crosslinking agent, and additives may be dissolved in a solvent, thereby being prepared in the form of a monomer composition solution.

In this regard, as the applicable solvent, any solvent may be used without limitations in the constitution as long as it is able to dissolve the above components. For example, one or more selected from water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, and N,N-dimethylacetamide may be used in combination.

The solvent may be included in a residual amount excluding the above-described components from the total weight of the monomer composition.

Meanwhile, the method of forming the water-containing gel polymer by thermal polymerization or photo-polymerization of the monomer composition is not particularly limited in the constitution, as long as it is a polymerization method generally used.

Specifically, the polymerization method is largely classified into the thermal polymerization and the photo-polymerization according to a polymerization energy source. The thermal polymerization may be commonly carried out in a reactor like a kneader equipped with agitating spindles whereas the photo-polymerization may be carried out in a reactor equipped with a movable conveyor belt. The above-described polymerization method is an example only, and the present invention is not limited to the above-described polymerization methods.

For example, the water-containing gel polymer may be obtained by performing thermal polymerization while providing hot air to the above-described reactor like a kneader equipped with the agitating spindles or heating the reactor. The water-containing gel polymer may have a size of centimeters or millimeters when it is discharged from an outlet of the reactor, according to the type of agitating spindles equipped in the reactor. Specifically, the size of the obtained water-containing gel polymer may vary depending on a concentration of the monomer composition fed thereto, a feeding speed or the like, and the water-containing gel polymer having a weight average particle size of 2 mm to 50 mm may be generally obtained.

Further, as described above, when the photo-polymerization is carried out in a reactor equipped with a movable conveyor belt, the obtained water-containing gel polymer may be usually a sheet-like water-containing gel polymer having a width of the belt. In this case, the thickness of the polymer sheet may vary depending on the concentration of the monomer composition fed thereto and the feeding speed. Usually, it is preferable to supply the monomer composition so that a sheet-like polymer having a thickness of about 0.5 cm to about 5 cm may be obtained. When the monomer composition is supplied to such an extent that the thickness of the sheet-like polymer becomes too thin, it is undesirable because the production efficiency is low, and when the thickness of the sheet-like polymer is more than 5 cm, the polymerization reaction may not evenly occur over the entire thickness because of the excessive thickness.

The water-containing gel polymer obtained by the above-mentioned method may have a water content of 40% by weight to 80% by weight. Meanwhile, the "water content" as used herein means a weight occupied by water with respect to the total weight of the water-containing gel polymer, which may be a value obtained by subtracting the weight of the dried polymer from the weight of the water-containing gel polymer. Specifically, the water content may be defined as a value calculated by measuring the weight loss due to evaporation of moisture in the polymer during the process of drying by raising the temperature of the polymer through infrared heating. At this time, the water content is measured under the drying conditions determined as follows: the drying temperature is increased from room temperature to about 180° C. and then the temperature is maintained at 180° C., and the total drying time is set to 20 minutes, including 5 minutes for the temperature rising step.

Next, the step of drying the obtained water-containing gel polymer may be performed.

At this time, a coarsely pulverizing step may be further carried out before drying, in order to increase the efficiency of the drying step, if necessary.

In this regard, a pulverizer used here is not limited by its configuration, and specifically, it may include any one selected from the group consisting of a vertical pulverizer, a turbo cutter, a turbo grinder, a rotary cutter mill, a cutter mill, a disc mill, a shred crusher, a crusher, a chopper, and a disc cutter, but is not limited to the above-described examples.

In this regard, the pulverizing step may be carried out so that the particle diameter of the water-containing gel polymer becomes about 2 mm to about 10 mm.

Pulverizing of the water-containing gel polymer into a particle diameter of less than 2 mm is technically not easy due to its high water content, and an agglomeration phenomenon between the pulverized particles may occur. Meanwhile, if the polymer is pulverized into a particle diameter of greater than 10 mm, the effect of increasing the efficiency in the subsequent drying step may be insignificant.

The water-containing gel polymer pulverized as above or the water-containing gel polymer immediately after polymerization without the pulverizing step is subjected to a drying step. In this case, the drying temperature of the drying step may be about 150° C. to about 250° C. When the drying temperature is lower than 150° C., it is apprehended that the drying time becomes too long and the physical properties of the superabsorbent polymer finally formed are deteriorated, and when the drying temperature is higher than 250° C., only the surface of the polymer is excessively dried, and thus it is apprehended that fine particles are generated during the subsequent pulverizing step, and the physical properties of the superabsorbent polymer finally formed may be deteriorated. Therefore, the drying may be preferably carried out at a temperature of about 150° C. to about 200° C., and more preferably at about 160° C. to about 180° C.

Meanwhile, the drying time may be about 20 minutes to about 90 minutes, taking into consideration the process efficiency, etc., but it is not limited thereto.

In the drying step, the drying method may also be selected and used without being limited by its constitution, as long as it is a method generally used for drying the water-containing gel polymer. Specifically, the drying step may be carried out by a method such as hot air supply, infrared irradiation, microwave irradiation, ultraviolet irradiation, etc. After the drying step as above is carried out, the water content of the polymer may be about 0.1% by weight to about 10% by weight.

Subsequently, the dried polymer obtained through the drying step is subjected to a pulverizing step.

The polymer powder obtained through the pulverizing step may have a particle diameter of about 150 μm to about 850 μm. Specific examples of a pulverizer that may be used to achieve the above particle diameter may include a pin mill, a hammer mill, a screw mill, a roll mill, a disc mill, a jog mill, etc., but the present invention is not limited to the above-described examples.

Also, in order to manage the physical properties of the superabsorbent polymer powder finally commercialized after the pulverizing step, the polymer powder obtained after the pulverization may undergo a separate step of size-sorting the polymer depending on the particle diameter. The polymer powder may be size-sorted at a predetermined weight ratio according to the range of the particle size.

Next, the base resin is mixed with the inorganic filler and the epoxy-based surface crosslinking agent (step 2).

In the general method of preparing the superabsorbent polymer, the dried and pulverized polymer, i.e., the base resin is mixed with a surface crosslinking solution including a surface crosslinking agent, and then the temperature of this mixture is increased by heating, thereby performing a surface crosslinking reaction of the pulverized polymer.

The surface crosslinking step is a step of forming the superabsorbent polymer having more improved physical properties by inducing a crosslinking reaction on the surface of the pulverized polymer in the presence of the surface crosslinking agent. Through this surface crosslinking, a surface-crosslinked layer (surface-modified layer) is formed on the surface of the pulverized polymer particles.

In general, since the surface crosslinking agent is applied on the surface of the superabsorbent polymer particles, the surface crosslinking reaction occurs on the surface of the superabsorbent polymer particles, resulting in improved crosslinkability on the surface of the particles while not substantially affecting the interior of the particles. Hence, the surface-crosslinked superabsorbent polymer particles has a higher degree of crosslinking near the surface thereof than the interior thereof.

Meanwhile, the surface crosslinking agent may be a compound that is reactable with a functional group of the polymer, and for example, a polyhydric alcohol compound, an epoxy compound, a polyamine compound, a haloepoxy compound, a condensate of a haloepoxy compound, oxazoline compounds, a multivalent metal salt, an alkylene carbonate compound, etc. is known to be used.

Meanwhile, according to the preparation method of the present invention, the epoxy-based surface crosslinking agent is used, and two kinds of epoxy-based surface crosslinking agents having different epoxy equivalent weights may be used in a mixture. When the two kinds of the epoxy-based surface crosslinking agents is used in a mixture, a crosslinked layer is is formed as a double layer on the surface of the superabsorbent polymer, and as a results, the rewetting property of the superabsorbent polymer may not be deteriorated, and liquid permeability which is a property of quickly passing water may be further improved.

Specifically, in the preparation method of the present invention, a first epoxy crosslinking agent having an epoxy equivalent weight of 100 g/eq or more to less than 130 g/eq and a second epoxy crosslinking agent having an epoxy equivalent weight of 130 g/eq to 200 g/eq are used as the epoxy-based surface crosslinking agent.

In a specific embodiment, the first epoxy crosslinking agent may have an epoxy equivalent weight in the range of 110 g/eq to 125 g/eq. The first epoxy crosslinking agent is used in order to obtain the effect of improving the overall absorption properties through the first surface crosslinking of the base resin. If the epoxy equivalent weight of the first epoxy crosslinking agent is less than 100 g/eq, it is difficult to secure the above-described effects.

The first epoxy crosslinking agent is preferably a bifunctional crosslinking agent. When a bifunctional epoxy crosslinking agent is used as the first epoxy crosslinking agent, flexibility of crosslinking chains may be secured, and as a result, absorption performances of the superabsorbent polymer may be maximized.

Further, a content of the first epoxy crosslinking agent may be 0.01 part by weight to 0.1 part by weight, or 0.02 parts by weight to 0.05 parts by weight with respect to 100 parts by weight of the base resin. If the content of the first epoxy crosslinking agent is less than 0.01 part by weight with respect to 100 parts by weight of the base resin, sufficient surface crosslinking may not proceed, and thus there is a problem in that absorbency under pressure and liquid permeability may be reduced. If the content exceeds 0.1 part by weight, there is a problem in that the rewetting property of the superabsorbent polymer may be reduced.

Examples of the first epoxy crosslinking agent may include one or more selected from the group consisting of ethyleneglycol diglycidyl ether and diethyleneglycol diglycidyl ether.

The second epoxy crosslinking agent has a higher epoxy equivalent weight than the first epoxy crosslinking agent, and at the time of surface crosslinking of the base resin, a penetration depth of the second epoxy crosslinking agent is different from that of the first epoxy crosslinking agent. Therefore, when the surface crosslinking is performed using the first epoxy crosslinking agent and the second epoxy crosslinking agent at the same time, the double crosslinking effect of the surface of the base resin is obtained.

In one embodiment, the epoxy equivalent weight of the second epoxy crosslinking agent may be 135 g/eq or more, 150 g/eq or more, or 160 g/eq or more and 195 g/eq or less, or 190 g/eq or less, but is not limited thereto.

A content of the second epoxy crosslinking agent may be 0.001 part by weight to 0.1 part by weight, or 0.005 parts by weight to 0.05 parts by weight with respect to 100 parts by weight of the base resin. If the content of the second epoxy crosslinking agent is less than 0.001 part by weight with respect to 100 parts by weight of the base resin, the double surface crosslinking effect may not be obtained. If the content exceeds 0.1 part by weight, the surface crosslinking strength is too strong, and thus there is a problem in that the rewetting property may be reduced.

Examples of the second epoxy crosslinking agent may include one or more selected from the group consisting of glycerol polyglycidyl ether, diglycerol polyglycidyl ether, polyglycerol polyglycidyl ether, and sorbitol polyglycidyl ether. The polyglycerol polyglycidyl ether may be preferably a triglycerol polyglycidyl ether having three repeating units.

The second epoxy crosslinking agent may preferably include three or more epoxy functional groups, or three to four epoxy functional groups. When the second epoxy crosslinking agent meeting the above number of the functional group is used, only the crosslinking strength of the outermost surface of the superabsorbent polymer particles may be additionally improved, and as a result, the liquid permeability and rewetting property of the superabsorbent polymer may be further enhanced.

When the epoxy-based surface crosslinking agent is added, it is additionally mixed with water, and then added in the form of a surface crosslinking solution. When water is added, it is advantageous in that the surface crosslinking agent may be evenly dispersed in the polymer. At this time, a content of water to be added may be preferably about 1 part by weight to about 10 parts by weight with respect to 100 parts by weight of the polymer in order to induce uniform dispersion of the surface crosslinking agent, to prevent agglomeration of the polymer powder, and at the same time, to optimize the surface penetration depth of the surface crosslinking agent.

Meanwhile, in addition to the above-described surface crosslinking agent, a multivalent metal salt, for example, an aluminum salt, more specifically, one or more selected from the group consisting of sulfates, potassium salts, ammonium salts, sodium salts, and hydrochloride salts of aluminum may be further included.

As the multivalent metal salt is additionally used, the liquid permeability of the superabsorbent polymer prepared by the method of one embodiment may be further improved. The multivalent metal salt may be added, together with the surface crosslinking agent, to the surface crosslinking solution, and may be used in an amount of 0.01 parts by weight to 4 parts by weight with respect to 100 parts by weight of the base resin.

Further, in the preparation method of the present invention, the inorganic filler is mixed with the base resin to provide an anti-caking effect, before raising the temperature for the surface modification reaction. In the present invention, the inorganic filler is dry-mixed, before mixing with the surface crosslinking solution, and in this case, the base resin and the inorganic filler may be more uniformly mixed.

The inorganic filler may be either hydrophobic or hydrophilic, and for example, silica particles such as fumed silica, precipitated silica, etc. may be used, but the present invention is not limited thereto.

Further, the inorganic filler may be added in an amount of about 0.01 part by weight to about 0.5 parts by weight, or about 0.02 parts by weight to about 0.2 parts by weight with respect to 100 parts by weight of the base resin or the superabsorbent polymer. When the use of the inorganic filler exceeds 0.5 parts by weight, absorption properties such as absorbency under pressure may be deteriorated, and when the use of the inorganic filler is less than 0.01 part by weight, the effect of preventing agglomeration may not be obtained. In this respect, the inorganic filler may be preferably used in the above range of part by weight.

Meanwhile, absorbency under pressure and liquid permeability may be improved by the surface crosslinking reaction, but it is necessary to further enhance the rewetting property.

According to the preparation method of the present invention, before raising the temperature in order to perform surface crosslinking reaction by mixing the base resin with the surface crosslinking agent, the base resin is mixed with a hydrophobic material, thereby further enhancing the rewetting property. The surface crosslinking efficiency may also be improved, thereby further enhancing absorption rate and liquid permeability, as compared with a resin of using no hydrophobic material.

As the hydrophobic material, a material having HLB meeting the lower limit of 0 or more, or 1 or more, or 2 or more, and the upper limit of 6 or less, or 5 or less, or 5.5 or less may be used. Further, since the hydrophobic material must be melted during the surface crosslinking reaction and be placed in the surface-modified layer of the base resin, a material having a melting point lower than the surface crosslinking reaction temperature may be used.

Examples of the applicable hydrophobic material may include glyceryl stearate, glycol stearate, magnesium stearate, glyceryl laurate, sorbitan stearate, sorbitan trioleate, PEG-4 dilaurate, etc., and preferably, glyceryl stearate or glyceryl laurate may be used, but the present invention is not limited thereto.

The hydrophobic material is distributed in the surface-modified layer of the surface of the base resin to prevent agglomeration or aggregation between the swelled resin particles due to the increased pressure when the superabsorbent polymer swells by absorbing a liquid, and the hydrophobic material provides the surface with hydrophobicity, thereby further facilitating liquid permeation and diffusion. Therefore, the hydrophobic material may contribute to improving the rewetting property of the superabsorbent polymer.

The hydrophobic material may be mixed in an amount of about 0.001 part by weight or more, or about 0.005 parts by weight or more, or about 0.01 part by weight or more and about 0.5 parts by weight or less, or about 0.3 parts by weight or less, or about 0.1 parts by weight or less with respect to 100 parts by weight of the base resin. If the content of the hydrophobic material is too small, it may be insufficient to improve rewetting properties. If the content of the hydrophobic material is too large, the base resin and the hydrophobic material may be detached from each other, and thus there is a problem in that the effect of improving the rewetting property may not be obtained or it may act as an impurity. In this respect, the hydrophobic material may be preferably used in the above range of part by weight.

A method of mixing the hydrophobic material with the base resin is not particularly limited. However, when the hydrophobic material is dispersed together with the surface crosslinking agent in the surface crosslinking 1 solution and mixed with the base resin, the hydrophobic material may be more uniformly coated on the superabsorbent polymer particles.

Next, the step of surface-modifying the base resin may be performed by raising the temperature of the mixture of the base resin and the epoxy-based surface crosslinking agent by heating (step 3).

The surface modification step may be performed by heating at a temperature of about 120° C. to about 190° C., preferably about 130° C. to about 180° C. for about 10 minutes to about 90 minutes, preferably about 20 minutes to about 70 minutes. If the crosslinking reaction temperature is lower than 120° C. or the reaction time is too short, the surface crosslinking reaction does not properly occur and thus permeability may be reduced, and if the crosslinking reaction temperature is higher than 190° C. or the reaction time is too long, there is a problem in that centrifuge retention capacity may be reduced.

A means for raising the temperature for surface modification reaction is not particularly limited. Heating may be performed by providing a heating medium or by directly providing a heat source. In this regard, the kind of the heating medium applicable may be a hot fluid such as steam, hot air, hot oil or the like, but the present invention is not limited thereto. The temperature of the heating medium to be provided may be properly controlled, taking into consideration the means of the heating medium, the heating rate, and the target temperature. Meanwhile, as the heat source to be directly provided, an electric heater or a gas heater may be used, but the present invention is not limited to these examples.

By the above surface modification step, a double surface crosslinked structure formed by reacting two different kinds of epoxy-based surface cros slinking agents with the functional groups of the base resin is formed on the surface of the base resin. Inside this surface-crosslinked structure, a surface-modified layer in which the above-described hydrophobic material and inorganic filler are uniformly distributed may be formed.

Therefore, due to the double surface-modified layer, the superabsorbent polymer prepared by the preparation method of the present invention may have improved rewetting and liquid permeability without deterioration in the physical properties such as centrifuge retention capacity and absorbency under pressure.

Accordingly, another embodiment of the present invention provides the superabsorbent polymer including the base resin including the crosslinked polymer which is prepared by crosslinking polymerization of the acrylic acid-based monomer having acidic groups, of which at least a part is neutralized; and the double surface-modified layer which is formed on the particle surface of the base resin, and is prepared by additionally crosslinking the crosslinked polymer via two kinds of epoxy-based surface crosslinking agents having different epoxy equivalent weights, wherein the surface-modified layer includes an inorganic filler, and the two kinds of epoxy-based surface crosslinking agents include the first epoxy crosslinking agent having an epoxy equivalent weight of 100 g/eq or more to less than 130 g/eq and the second epoxy crosslinking agent having an epoxy equivalent weight of 130 g/eq to 200 g/eq.

Detailed descriptions of a specific method of preparing the superabsorbent polymer and physical properties thereof are the same as those described in the method of preparing the superabsorbent polymer.

The superabsorbent polymer may have centrifuge retention capacity (CRC) in the range of about 25 g/g or more, or about 29 g/g or more, or about 30 g/g or more and about 40 g/g or less, or about 38 g/g or less, or about 35 g/g or less, as measured in accordance with the EDANA method WSP 241.3.

Further, the superabsorbent polymer may have absorbency under pressure (AUP) (0.3 psi) in the range of about 20 g/g or more, or about 23 g/g or more, or about 25 g/g or more and about 37 g/g or less, or about 35 g/g or less, or about 32 g/g or less, as measured in accordance with the EDANA method WSP 242.3.

Further, the superabsorbent polymer may have an absorption rate (vortex time) of 40 seconds or less, or 35 seconds or less, or about 32 seconds or less. As the value of the absorption rate is smaller, it means more excellent absorption rate. Therefore, the lower limit of the absorption rate is theoretically 0 second, but it may be, for example, about 5 seconds or more, or about 10 seconds or more, or about 12 seconds or more.

The absorption rate means a time (unit; sec) taken for a vortex of liquid to disappear by rapid absorption when the superabsorbent polymer in physiological saline is stirred. As the time is shorter, the superabsorbent polymer may be determined to have a faster initial absorption rate.

Further, the superabsorbent polymer may have liquid permeability (unit; sec) of about 35 seconds or less, or about 30 seconds or less, as measured according to the following Equation 1. As the value of the liquid permeability is smaller, it means more excellent liquid permeability. Therefore, the theoretical lower limit is 0 second, but it may be, for example, about 5 seconds or more, or about 10 seconds or more, or about 12 seconds or more.

$$\text{Liquid permeability (sec)} = T1 - B \qquad \text{[Equation 1]}$$

in Equation 1, T1 represents the time taken for the liquid level to decrease from 40 ml to 20 ml, when 0.2±0.0005 g of the size-sorted superabsorbent polymer sample (300 μm~600 μm) is put in a chromatography column, brine is applied thereto at a volume of 50 ml, and then left for 30 minutes, and B represents the time taken for the liquid level in the brine-filled chromatography column to decrease from 40 ml to 20 ml.

Further, the superabsorbent polymer may exhibit more improved rewetting property while exhibiting excellent absorption properties.

More specifically, the superabsorbent polymer may have the rewetting property (long-term tap water rewetting under pressure) of 1.0 g or less, or 0.9 g or less, or 0.8 g or less, the rewetting property defined by the weight of water that soaks out from the superabsorbent polymer to a filter paper, when 4 g of the superabsorbent polymer is immersed in 200 g of tap water and allowed to swell for 2 hours, and then the swollen superabsorbent polymer is left on the filter paper under a pressure of 0.75 psi for 1 minute. As the weight of the water is smaller, it means more excellent rewetting property. Therefore, the theoretical lower limit is 0 second, but it may be, for example, 0.1 g or more, or 0.2 g or more, or 0.3 g or more.

The tap water used in the evaluation of the rewetting property has conductivity of 140 μS/cm to 150 μS/cm. Since the conductivity of tap water greatly influences the properties to be measured, it is necessary to measure the physical properties such as rewetting property by using tap water having conductivity equivalent thereto.

As described above, the superabsorbent polymer of the present invention may have excellent absorbency and may suppress rewetting and urine leakage phenomena even at the time of absorbing a large amount of urine.

The present invention will be described in more detail with reference to the following Examples. However, the following Examples are only for illustrating the present invention, and the detailed description of the present invention is not limited by the following Examples.

EXAMPLE

Preparation of Superabsorbent Polymer

Example 1

(1) Preparation of Base Resin 518 g of acrylic acid, 3.2 g of polyethylene glycol diacrylate (polyethyleneglycol (400) diacrylate), and 0.04 g of diphenyl(2,4,6-trimethylbenzoyl)-phosphine oxide were added to a 3 L glass container equipped with a stirrer, a nitrogen feeder, and a thermometer, and dissolved. Then, 822.2 g of 24.5% sodium hydroxide solution was added thereto and nitrogen was continuously injected to prepare a water-soluble unsaturated monomer aqueous solution. The water-soluble unsaturated monomer aqueous solution was cooled to 40° C. 500 g of this aqueous solution was fed to a stainless steel container having a width of 250 mm, a length of 250 mm, and a height of 30 mm, and UV polymerization was performed by UV radiation (exposure dose: 10 mV/cm$^2$) for 90 seconds to obtain a water-containing gel polymer. The water-containing gel polymer thus obtained was pulverized to a size of 2 mm*2 mm, and spread as thick as about 30 mm on a stainless wire gauze having a hole size of 600 μm and dried in a hot air oven at 180° C. for 30 minutes. The dry polymer thus obtained was pulverized with a pulverizer, and then size-sorted through an ASTM standard sieve to obtain a base resin having a particle size of 150 μm to 850 μm.

(2) Preparation of Superabsorbent Polymer 100 parts by weight of the base resin was dry-mixed with 0.1 part by weight of silica, and then a surface crosslinking solution containing 0.02 parts by weight of ethylene glycol diglycidyl ether (epoxy equivalent weight of 113~125 g/eq), 0.01 part by weight of glycerol polyglycidyl ether (epoxy equivalent weight of 135~155 g/eq, trifunctional), 6.2 parts by weight of water, 0.2 parts by weight of aluminum sulfate, and 0.03 parts by weight of glyceryl stearate (HLB 3.8) was sprayed thereto and mixed therewith. This mixture was put in a container equipped with a stirrer and a double jacket, and a surface crosslinking reaction was performed at 140° C. for 35 minutes. Thereafter, the surface-treated powder was size-sorted through an ASTM standard sieve to obtain a superabsorbent polymer powder having a particle size of 150 μm to 850 μm.

Example 2

A superabsorbent polymer powder was obtained in the same manner as in Example 1, except that glycerol polyglycidyl ether was used in an amount of 0.005 parts by weight with respect to 100 parts by weight of the base resin in step (2).

Example 3

A superabsorbent polymer powder was obtained in the same manner as in Example 1, except that glycerol polyglycidyl ether was used in an amount of 0.03 parts by weight with respect to 100 parts by weight of the base resin in step (2).

Example 4

A superabsorbent polymer powder was obtained in the same manner as in Example 1, except that glycerol polyglycidyl ether was used in an amount of 0.05 parts by weight with respect to 100 parts by weight of the base resin in step (2).

Example 5

A superabsorbent polymer powder was obtained in the same manner as in Example 1, except that polyglycerol polyglycidyl ether (epoxy equivalent weight of 168 g/eq), instead of glycerol polyglycidyl ether, was used in an amount of 0.01 part by weight with respect to 100 parts by weight of the base resin in step (2).

Example 6

A superabsorbent polymer powder was obtained in the same manner as in Example 1, except that sorbitol polyglycidyl ether (epoxy equivalent weight 160~190 g/eq), instead of glycerol polyglycidyl ether, was used in an amount of 0.01 part by weight with respect to 100 parts by weight of the base resin in step (2).

Comparative Example 1

(1) Preparation of Base Resin 518 g of acrylic acid, 3.2 g of polyethylene glycol diacrylate (polyethyleneglycol (400) diacrylate), and 0.04 g of diphenyl(2,4,6-trimethylbenzoyl)-phosphine oxide were added to a 3 L glass container equipped with a stirrer, a nitrogen feeder, and a thermometer, and dissolved. Then, 822.2 g of 24.5% sodium hydroxide solution was added thereto and nitrogen was continuously injected to prepare a water-soluble unsaturated monomer aqueous solution. The water-soluble unsaturated monomer aqueous solution was cooled to 40° C. 500 g of this aqueous solution was fed to a stainless steel container having a width of 250 mm, a length of 250 mm, and a height of 30 mm, and UV polymerization was performed by UV radiation (exposure dose: 10 10 mV/cm$^2$) for 90 seconds to obtain a water-containing gel polymer. The water-containing gel polymer thus obtained was pulverized to a size of 2 mm*2 mm, and spread as thick as about 30 mm on a stainless wire gauze having a hole size of 600 μm and dried in a hot air oven at 180° C. for 30 minutes. The dry polymer thus obtained was pulverized with a pulverizer, and then size-sorted through an ASTM standard sieve to obtain a base resin having a particle size of 150 μm to 850 μm.

(2) Preparation of Superabsorbent Polymer 100 parts by weight of the base resin was dry-mixed with 0.1 part by weight of silica, and then a surface crosslinking solution containing 0.02 parts by weight of ethylene glycol diglycidyl ether (epoxy equivalent weight of 113~125 g/eq), 6.2 parts by weight of water, 0.2 parts by weight of aluminum sulfate, and 0.03 parts by weight of glyceryl stearate (HLB 3.8) was sprayed thereto and mixed therewith. This mixture was put in a container equipped with a stirrer and a double jacket, and a surface crosslinking reaction was performed at 140° C. for 35 minutes. Thereafter, the surface-treated powder was size-sorted through an ASTM standard sieve to obtain a superabsorbent polymer powder having a particle size of 150 μm to 850 μm.

Comparative Example 2

A superabsorbent polymer powder was obtained in the same manner as in Comparative Example 1, except that ethylene glycol diglycidyl ether was used in an amount of 0.03 parts by weight with respect to 100 parts by weight of the base resin in step (2).

Comparative Example 3

A superabsorbent polymer powder was obtained in the same manner as in Comparative Example 1, except that ethylene glycol diglycidyl ether was used in an amount of 0.05 parts by weight with respect to 100 parts by weight of the base resin in step (2).

Experimental Example

Physical properties were evaluated for the superabsorbent polymers prepared in Examples and Comparative Examples by the following methods.

Unless otherwise indicated, the following physical properties were all evaluated at constant temperature and humidity (23±1° C., relative humidity of 50±10%), and physiological saline or brine means a 0.9 wt % sodium chloride (NaCl) aqueous solution.

Further, tap water used in the following evaluation of the rewetting property was tap water having a conductivity of 140 μS/cm to 150 μS/cm, as measured using Orion Star A222 (company: Thermo Scientific).

(1) Centrifuge Retention Capacity (CRC)

The centrifuge retention capacity by absorption capacity under no load was measured for each polymer in accordance with EDANA WSP 241.3.

In detail, after uniformly introducing $W_0(g)$ (about 0.2 g) of the superabsorbent polymer in a nonwoven fabric-made bag and sealing the same, it was immersed in physiological saline (0.9 wt %) at room temperature. After 30 minutes, the bag was dehydrated by using a centrifuge at 250 G for 3 minutes, and then the weight $W_2(g)$ of the bag was measured. Further, after carrying out the same operation without using the polymer, the weight $W_1(g)$ of the bag was measured. CRC (g/g) was calculated using each obtained weight according to the following Equation.

$$\text{CRC (g/g)} = \{[W_2(g) - W_1(g)]/W_0(g)\} - 1 \qquad \text{[Equation 1]}$$

(2) Absorption Rate (Vortex Time)

The absorption rate (vortex time) was measured in seconds according to the method described in International Publication WO 1987-003208.

Specifically, 2 g of the superabsorbent polymer was added to 50 mL of physiological saline at 23° C., and stirred with a magnetic bar (diameter of 8 mm and length of 30 mm) at 600 rpm, and a time taken for vortex to disappear was measured in seconds to calculate the vortex time.

(3) Absorbency Under Pressure (AUP)

The absorbency under pressure of 0.3 psi was measured for each polymer in accordance with EDANA WSP 242.3.

In detail, a 400 mesh stainless steel net was installed in the cylindrical bottom of a plastic having an internal diameter of 60 mm $W_0(g)$ (0.90 g) of the superabsorbent polymer was uniformly scattered on the steel net under conditions of room temperature and relative humidity of 50%, and a piston capable of uniformly providing a load of 0.3 psi was put thereon, in which an external diameter of the piston was slightly smaller than 60 mm, there was no gap between the internal wall of the cylinder and the piston, and the jig-jog of the cylinder was not interrupted. At this time, the weight $W_3(g)$ of the apparatus was measured.

After putting a glass filter having a diameter of 90 mm and a thickness of 5 mm in a petri dish having a diameter of 150 mm, a physiological saline composed of 0.9% by weight of sodium chloride was poured until the surface level of the physiological saline became equal to the upper surface of the glass filter. A sheet of filter paper having a diameter of 90 mm was put on thereon. The measurement apparatus was mounted on the filter paper, thereby getting the liquid absorbed under the load for 1 hour. 1 hour later, the weight $W_4(g)$ was measured after lifting the measurement apparatus up.

Absorbency under pressure (g/g) was calculated using the obtained weights according to the following Equation:

$$AUP(g/g)=[W_4(g)-W_3(g)]/W_0(g) \quad \text{[Equation 2]}$$

(4) Liquid Permeability

Lines were marked on the liquid levels of 20 ml and 40 ml in a chromatography column (F20 mm) with a piston. Thereafter, in order to prevent bubbles between a glass filter and a cock at the bottom of the chromatography column, water was injected upward and filled up to about 10 ml, and the column was washed 2~3 times with brine, and 0.9% brine was filled up to 40 ml or more. The piston was placed in the chromatography column, and the lower valve was opened to record the time (B) at which the liquid level decreased from the marked line of 40 ml to the marked line of 20 ml.

10 ml of brine was left in the chromatography column, 0.2±0.0005 g of the size-sorted superabsorbent polymer sample (300 to 600 μm) was added thereto, and brine was added up to 50 ml, and left for 30 minutes. Thereafter, a piston with a weight (0.3 psi=106.26 g) was placed in the chromatography column, and left for 1 minute. Then, the lower valve of the chromatography column was opened to record the time (T1) at which the liquid level decreased from the marked line of 40 ml to the marked line of 20 ml. The time (unit: second) of T1–B was calculated.

(5) Long-Term Tap Water Rewetting Under Pressure (2 hrs)

① 4 g of the superabsorbent polymer was uniformly scattered on a petri dish with a diameter of 13 cm, and then 200 g of tap water was poured and allowed to swell for 2 hours.

② The superabsorbent polymer swollen for 2 hours was put on 20 sheets of filter paper (manufacturer: whatman, catalog No. 1004-110, pore size: 20-25 μm, diameter: 11 cm), and a weight of 5 kg (0.75 psi) with a diameter of 11 cm was applied thereto for 1 minute.

③ After applying the weight for 1 minute, the amount (unit: g) of tap water soaked into the filter paper was measured.

The values of the physical properties of Examples and Comparative Examples are described in Table 1 below.

TABLE 1

|  | CRC (g/g) | Vortex time (sec) | 0.3 psi AUP (g/g) | Liquid permeability (sec) | Long-term tap water rewetting under pressure (g) |
|---|---|---|---|---|---|
| Example 1 | 30.3 | 26 | 28.5 | 25 | 0.67 |
| Example 2 | 30.4 | 28 | 27.7 | 27 | 0.73 |
| Example 3 | 30.1 | 28 | 28.7 | 17 | 0.72 |
| Example 4 | 29.5 | 27 | 28.4 | 15 | 0.85 |
| Example 5 | 30.5 | 31 | 27.0 | 28 | 0.70 |
| Example 6 | 30.4 | 31 | 27.2 | 30 | 0.75 |
| Comparative Example 1 | 30.9 | 32 | 26.6 | 43 | 0.73 |
| Comparative Example 2 | 30.1 | 31 | 28.1 | 37 | 0.84 |
| Comparative Example 3 | 29.8 | 29 | 27.6 | 31 | 1.12 |

Referring to Table 1, it was confirmed that Examples 1 to 6 of the present invention all exhibited excellent rewetting property and liquid permeability. In contrast, Comparative Examples 1 to 2, in which only the first epoxy crosslinking agent having an epoxy equivalent weight of 100 g/eq or more to less than 130 g/eq was used, exhibited poor liquid permeability and rewetting property, as compared with Examples. In other words, it was confirmed that when the equal amount of epoxy-based surface crosslinking agent was used, Examples exhibited excellent liquid permeability and rewetting property, as compared with Comparative Examples.

The invention claimed is:

1. A method of preparing a superabsorbent polymer, comprising:
    preparing a base resin by crosslinking polymerization of an acrylic acid-based monomer having acidic groups, of which at least a part is neutralized, and an internal crosslinking agent;
    preparing a surface crosslinking solution by dry-mixing the base resin with an inorganic filler and, subsequently, mixing with an epoxy-based surface crosslinking agent by dissolving in water to form the surface crosslinking solution; and
    performing surface modification of the base resin by raising the temperature of the surface crosslinking solution,
    wherein the epoxy-based surface crosslinking agent includes a first epoxy crosslinking agent having an epoxy equivalent weight of 100 g/eq or more to less than 130 g/eq and a second epoxy crosslinking agent having an epoxy equivalent weight of 130 g/eq to 200 g/eq.

2. The method of claim 1, wherein the first epoxy crosslinking agent is included in an amount of 0.01 part by weight to 0.1 part by weight with respect to 100 parts by weight of the base resin, and the second epoxy crosslinking agent is included in an amount of 0.001 part by weight to 0.1 part by weight with respect to 100 parts by weight of the base resin.

3. The method of claim 1, wherein the first epoxy crosslinking agent is one or more selected from the group consisting of ethyleneglycol diglycidyl ether and diethyleneglycol diglycidyl ether.

4. The method of claim 1, wherein the second epoxy crosslinking agent is one or more selected from the group consisting of glycerol polyglycidyl ether, diglycerol polyglycidyl ether, polyglycerol polyglycidyl ether, and sorbitol polyglycidyl ether.

5. The method of claim 1, wherein a hydrophobic material having HLB of 0 or more and 6 or less is further included during preparation of the surface crosslinking solution.

6. The method of claim 5, wherein the hydrophobic material includes one or more of glyceryl stearate, glycol stearate, magnesium stearate, glyceryl laurate, sorbitan stearate, sorbitan trioleate, or PEG-4 dilaurate.

7. The method of claim 5, wherein the hydrophobic material is mixed in an amount of 0.001 part by weight to 0.5 parts by weight with respect to 100 parts by weight of the base resin.

8. The method of claim 1, wherein the surface modification is performed at a temperature of 120° C. to 190° C.

9. The method of claim 1, wherein the preparing the base resin includes:
    forming a water-containing gel polymer by polymerizing a monomer composition including the acrylic acid-based monomer having acidic groups, of which at least a part is neutralized, the internal crosslinking agent, and a polymerization initiator;
    drying the water-containing gel polymer;
    pulverizing the dried polymer; and
    size-sorting the pulverized polymer.

10. A superabsorbent polymer comprising a base resin including a crosslinked polymer which is prepared by crosslinking polymerization of an acrylic acid-based monomer having acidic groups, of which at least a part is neutralized; and a double surface-modified layer which is formed on a particle surface of the base resin, and is prepared by additionally crosslinking the crosslinked polymer via two kinds of epoxy-based surface crosslinking agents having different epoxy equivalent weights, wherein the double surface-modified layer includes an inorganic filler, and the two kinds of epoxy-based surface crosslinking agents include a first epoxy crosslinking agent having an epoxy equivalent weight of 100 g/eq or more to less than 130 g/eq and a second epoxy crosslinking agent having an epoxy equivalent weight of 130 g/eq to 200 g/eq.

11. The superabsorbent polymer of claim 10, wherein the superabsorbent polymer has an absorption rate (vortex time) of 40 seconds or less.

12. The superabsorbent polymer of claim 10, wherein the superabsorbent polymer has a liquid permeability (unit: second) of 35 seconds or less, as measured according to the following Equation 1:

$$\text{Liquid permeability (sec)} = T1 - B \quad \text{[Equation 1]}$$

in Equation 1, T1 represents a time taken for a liquid level to decrease from 40 ml to 20 ml, when 0.2±0.0005 g of a size-sorted superabsorbent polymer sample (300 μm~600 μm) is put in a chromatography column, brine is applied thereto at a volume of 50 ml, and then left for 30 minutes, and B represents a time taken for a liquid level in a brine-filled chromatography column to decrease from 40 ml to 20 ml.

13. The superabsorbent polymer of claim 10, wherein the superabsorbent polymer has a centrifuge retention capacity (CRC) of 25 g/g or more.

14. The superabsorbent polymer of claim 10, wherein the superabsorbent polymer has a rewetting property (long-term tap water rewetting under pressure) of 1.0 g or less, the rewetting property defined by a weight of water that soaks out from the superabsorbent polymer to a filter paper, when 4 g of the superabsorbent polymer is immersed in 200 g of tap water and allowed to swell for 2 hours, and then the swollen superabsorbent polymer is left on the filter paper under a pressure of 0.75 psi for 1 minute.

* * * * *